United States Patent [19]

Itoh et al.

[11] Patent Number: 4,961,853
[45] Date of Patent: Oct. 9, 1990

[54] POROUS MEMBRANES AND PRODUCTION PROCESSES THEREOF

[75] Inventors: Hajime Itoh, Hiroshima; Kouzi Ohbori, Aichi; Kazutami Mitani, Hiroshima; Hiroshi Takahashi, Hiroshima; Kouji Takehashi, Hiroshima; Kunihiro Aoki, Hiroshima, all of Japan

[73] Assignee: Mitsubishi Rayon Co., Ltd., Tokyo, Japan

[21] Appl. No.: 378,571

[22] PCT Filed: Oct. 20, 1988

[86] PCT No.: PCT/JP88/01064
§ 371 Date: Jun. 23, 1989
§ 102(e) Date: Jun. 23, 1989

[87] PCT Pub. No.: WO89/04198
PCT Pub. Date: May 18, 1989

[30] Foreign Application Priority Data

Nov. 4, 1987 [JP] Japan ............................... 62-278733
Nov. 4, 1987 [JP] Japan ............................... 62-2787341

[51] Int. Cl.$^5$ ...................... B01D 67/00; B01D 69/00
[52] U.S. Cl. .................. 210/500.34; 264/45.1
[58] Field of Search ........ 525/243; 210/500.1, 210/500.21, 500.27, 500.28, 500.33, 500.34, 500.36, 500.4; 264/DIG. 48, DIG. 62, 41, 45.1, 48

[56] References Cited

U.S. PATENT DOCUMENTS 4,374,232 2/1983 Davis ................................ 525/243

FOREIGN PATENT DOCUMENTS 36-20742 10/1961 Japan .
53-8670 1/1978 Japan .
62-7401 1/1987 Japan .
62-14903 1/1987 Japan .
62-14904 1/1987 Japan .
62-114610 5/1987 Japan .
63-190602 8/1988 Japan .

Primary Examiner—Frank Sever
Attorney, Agent, or Firm—Oblon, Spivak, McClelland, Maier & Neustadt

[57] ABSTRACT

Disclosed are heat-resisting porous membranes or hydrophilized heat-resisting porous membranes comprising a polyolefin, especially a polyethylene or a polypropylene membrane having a crosslinked polymer held thereon, the crosslinked polymer being composed principally of (a) a polymerizable monomer containing one acid anhydride group or two esterified carboxyl groups or a monomer having at least one carboxylic group and (b) divinylbenzene, or of (a), (b) and further (c) styrene or a derivative thereof, or of (b) and (c). These membranes are prepared by thermally polymerizing some of monomer components from (a) through (c) held on at least a part of the surface of the porous membranes and optionally by further hydrophilizing the crosslinked polymer. The resulting porous membranes are useful for membrane separation requiring steam sterilization and for membrane separation of water of a high temperature.

9 Claims, 1 Drawing Sheet

POROUS MEMBRANES AND PRODUCTION PROCESSES THEREOF

DESCRIPTION

1. Technical Field

This invention relates to porous polyolefin membranes having excellent heat resistance or excellent heat resistance and hydrophilicity, as well as production processes thereof.

2. Background Art

With the recent development of industry, various types of separating membranes have come to be used in such fields as water purification, blood treatment, air cleaning and food industry. For example, microfilters are being utilized to obtain highly pure water or highly clean air. Among others, microfilter formed of a polyolefin such as polyethylene are being widely used because they are cheap, have excellent chemical resistance and exhibit good membrane properties such as strength, elongation and flexibility.

The field of application of microfilter is extending steadily and, at present, it is strongly desired to use them at elevated temperatures, for example, of the order of 80–95° C. Moreover, in certain applications of microfilter, their contamination with microorganisms such as bacteria and molds is not permitted and, therefore, they are sterilized by some means. Useful sterilizing processes include treatment with chemicals such as ethylene oxide, formalin and hydrogen peroxide, exposure to radiation such as gamma rays, and steam heating. Among them, steam heating is most desirable because of its effectiveness and simplicity. Usually, steam heating is done at 121° C. for about 30 minutes.

However, porous membranes formed of polyolefins such as polyethylene and polypropylene are very liable to heat shrinkage. When these porous membranes are heat-treated or used at high temperature, they undergo morphological changes. This causes a sharp reduction in water or air permeability and impairs their function as separating membranes. Moreover, since porous polyolefin membranes are hydrophobic, water cannot permeate therethrough when they are used in an untreated condition.

As a means for improving the heat resistance of porous polyolefin membranes, Japanese Patent Laid-Open No. 33878/'87 proposed a polyolefin hollow fiber membrane in which a heat-resisting polymer film having a crosslinked structure is formed on the surfaces thereof. Moreover, Japanese Patent Laid-Open No. 57836/'81 proposed a porous polyethylene membrane which is rendered hydrophilic by the introduction of sulfonic acid groups.

However, in the heat-resisting polyolefin hollow fiber membrane disclosed in Japanese Patent Laid-Open No. 33878/'87, the heat resistance of the polymer film itself is insufficient. The porous polyethylene membrane disclosed in Japanese Patent Laid-Open No. 57836/'81 is satisfactorily hydrophilic, but its heat resistance is insufficient.

Disclosure of the Invention

The primary object of the present invention is to provide a porous polyethylene or polypropylene membrane which has excellent heat resistance and can hence withstand steam sterilization and other heat treatments, a porous polyolefin membrane which is excellent in both heat resistance and hydrophilicity, and production processes thereof.

In one aspect of the present invention, there is provided a heat-resisting porous membrane comprising a porous polyethylene or polypropylene membrane having a crosslinked polymer held on at least a part of the surfaces thereof, the crosslinked polymer being composed principally of (a) a polymerizable monomer A containing one acid anhydride group or two esterified carboxyl groups and having reactivity ratios $r_1$ and $r_2$ of not greater than 0.30 for copolymerization reaction with styrene, (b) divinylbenzene and optionally (c) at least one of styrene and α-methylstyrene (hereinafter referred to as a styrene monomer).

In another aspect of the present invention, there is provided a process for the production of a heatresisting porous membrane which comprises the steps of holding a monomer mixture composed principally of (a) a polymerizable monomer A as defined above, (b) divinylbenzene and optionally (c) a styrene monomer, on at least a part of the surfaces of a starting porous membrane formed of polyethylene or polypropylene; and thermally polymerizing the monomer mixture.

In still another aspect of the present invention, there is provided a hydrophilized porous membrane comprising a porous polyolefin membrane having a crosslinked polymer held on at least a part of the surfaces thereof, the crosslinked polymer being composed principally of (d) monomer units D containing at least one carboxyl group, (b) divinylbenzene units and optionally (c) styrene monomer units and being characterized by a substantially uniform distribution of the monomer units D.

In a further aspect of the present invention, there is provided a process for the production of a hydrophilized porous membrane which comprises the steps of holding a monomer mixture composed principally of (a) a polymerizable monomer A as defined above, (b) divinylbenzene and optionally (c) a styrene monomer, on at least a part of the surfaces of a starting porous membrane formed of a polyolefin; heating the monomer mixture to form a crosslinked polymer; and hydrolyzing at least a part of the acid anhydride groups or esterified carboxyl groups present in the crosslinked polymer.

In a further aspect of the present invention, there is provided a heat-resisting porous membrane comprising a porous polyethylene or polypropylene membrane having a crosslinked polymer held on at least a part of the surfaces thereof, the crosslinked polymer being composed principally of (b) divinylbenzene and (c) a styrene monomer.

In a further aspect of the present invention, there is provided a process for the production of a heatresisting porous membrane which comprises the steps of holding a monomer mixture composed principally of (b) divinylbenzene and (c) a styrene monomer, on at least a part of the surfaces of a starting porous membrane formed of polyethylene or polypropylene; and thermally polymerizing the monomer mixture.

BEST MODE FOR CARRYING OUT THE INVENTION

Figure 1:
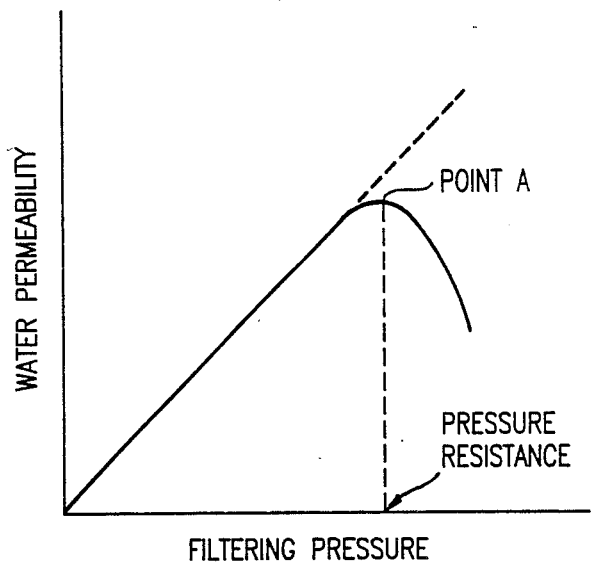
FIG. 1 is a graph serving to explaining the procedure for measuring the pressure resistance of a porous hollow fiber membrane.

The polyolefin material forming the porous polyolefin membrane used in the present invention can be a polymer or copolymer composed principally of one of more monomers selected from the group consisting or ethylene, propylene, 4-methyl-1-pentene and 3-methyl1-butene, or a fluorinated product thereof.

The starting porous membrane used to produce the porous membrane of the present invention may be in any form such as hollow fiber membrane, planar membrane or tubular membrane. Although porous membranes having various pore sizes can be used depending on the intended purpose, preferred examples thereof have a membrane thickness of about 20–200 µm, a porosity of about 20–90%, a water permeability of 0.001–10 l/m²·hr·mmHg as measured by the alcohol-dependent hydrophilizing method, and a pore diameter of about 0.01–5 µm.

As the starting porous membrane, there can be used porous membranes having pore structures formed by various methods including those in which a material is melt formed and then stretched and those in which a material containing an inorganic compound or an ester is melt formed and then leached. Among them, porous membranes obtained by melt forming and subsequent stretching process are preferably used because they have high porosity and are less liable to performance losses due to clogging. Porous membranes obtained by melt forming and subsequent stretching process have a pore structure in which minute slit-like spacings (pores) formed by microfibrils and knots communicated three-dimensionally with one another, and can be produced, for example, by the processes disclosed in U.S. Pat. Nos. 4,401,567 and 4,741,829.

With regard to the form of the starting porous membrane, hollow fiber membranes are preferably used because they have a large membrane area per unit volume.

Now, the crosslinked polymer (i) for imparting heat resistance to a porous membrane formed of polyethylene or polypropylene will be described hereinafter. This crosslinked polymer (i) may be composed of any of three combinations of monomer components: (1) a polymerizable monomer A, a styrene monomer and divinylbenzene, (2) a polymerizable monomer A and divinylbenzene, and (3) a styrene monomer and divinylbenzene. All of the crosslinked polymers (i) composed of these combinations of monomer components have good heat resistance and serve to impart heat resistance to porous membranes formed of polyethylene or polypropylene.

Industrially, divinylbenzene (b) is obtainable in the form of a mixture composed of 55–60% of divinylbenzene, 35–40% of ethylvinylbenzene, and 10% or less of saturated compounds. In the practice of the present invention, such a mixture or a more purified product can be used.

Typically, styrene is used as the styrene monomer (c).

The polymerizable monomer A should have a specific degree of reactivity for styrene. Its reactivity ratios $r_1$ and $r_2$ are defined by the following equations.

$$r_1 = Kp(St-St)/Kp(St-Ca)$$

$$r_2 = Kp(Ca-Ca)/Kp(St-Ca)$$

where
- $Kp(St-St)$: the reaction rate between styrene molecules,
- $Kp(St-Ca)$: the reaction rate between a styrene molecule and a polymerizable monomer A molecule, and
- $Kp(Ca-Ca)$: the reaction rate between polymerizable monomer A molecules.

Specific examples of the polymerizable monomer A include maleic anhydride, itaconic anhydride, hymic anhydride, maleic esters and fumaric esters. Among these compounds, maleic anhydride, di-n-propyl maleate, di-i-propyl maleate, di-2-ethylhexyl maleate, di-n-butyl maleate, di-t-butyl maleate, di-n-proyl fumarate, di-i-propyl propyl fumarate, di-n-butyl fumarate, di-t-butyl fumarate, dicyclopentyl fumarate, dicyclohexyl fumarate and di-2-ethylhexyl fumarate are especially preferred.

As described above, a two-component crosslinked polymer composed of a styrene monomer and divinylbenzene serves to impart a certain degree of heat resistance to a porous membrane. However, a crosslinked polymer containing a polymerizable monomer A having one acid anhydride group or two esterified carboxyl groups has better heat resistance and, therefore, its use makes it possible to impart the same degree of heat resistance to a porous membrane with a smaller amount held than the former crosslinked polymer. For this reason, the crosslinked polymer containing the polymerizable monomer A can impart heat resistance to a porous membrane while minimizing the reduction in the porosity of the porous membrane.

Moreover, since the polymerizable monomer A has reactivity ratios $r_1$ and $r_2$ of not greater than 0.30 for copolymerization reaction with styrene, almost no block polymer is formed in the polymerization system containing this monomer. In the resulting crosslinked polymer, therefore, the monomer components are evenly distributed in almost equal proportions on a molecular level. Accordingly, this crosslinked polymer has substantially uniform properties throughout its entire structure.

The hydrophilized porous membrane of the present invention is a porous membrane having heat resistance in addition to hydrophilicity. In this hydrophilized porous membrane, the monomer units constituting the crosslinked polymer (ii) held on the surfaces thereof serve to impart heat resistance to the porous membrane, and the monomer units D having at least one carboxyl group (preferably two carboxyl groups) serve to impart hydrophilicity to the porous membrane.

In this crosslinked polymer (ii), the monomer units D are substantially uniformly distributed. The term "substantially uniformly distributed" as used herein means that the monomer units D are substantially evenly distributed on a molecular level without forming any block copolymer. For this reason, every part of the crosslinked polymer exhibits hydrophilicity without variation.

Specific examples of the monomer unit D include monomer units derived from maleic acid, fumaric acid, itaconic acid and hymic acid.

Moreover, it is especially preferable that this crosslinked polymer have a structure in which the monomer units D are substantially alternately connected with the divinylbenzene units and, if present, the styrene monomer units. The monomer units D which can form such a structure include monomer units derived from maleic acid and its derivatives.

The term "at least a part of the surfaces" of the porous membrane of the present invention, on which a heat-resisting crosslinked polymer or a heat-resisting and hydrophilic crosslinked polymer is held, means a part or the whole of the pore walls and outer surfaces thereof. More specifically, the crosslinked polymer has only to be held to such an extent that the heat resistance of the porous membrane is substantially improved or that the porous membrane has a sufficient degree of hydrophilicity to permit the permeation of water under the commonly employed transmembrane pressure difference. It is not entirely necessary to cover the entire surfaces with the crosslinked polymer.

The term "held" as used herein means that the crosslinked polymer is firmly bound or attached to the pore walls to such an extent as not to come off easily during storage or use of the porous membrane. The crosslinked polymer may be chemically bonded to the pore walls, attached thereto by an anchoring effect, or held by a combination of chemical bonding and anchoring.

Especially where a porous membrane produced by the above-described stretching method is used as the starting porous membrane, the crosslinked polymer is formed so as to surround the microfilbrils and, therefore, can be held firmly. Accordingly, it is preferable to use a porous membrane produced by the stretching method as the starting porous membrane.

The amount of the heat-resisting crosslinked polymer (i) or heat-resisting and hydrophilic crosslinked polymer (ii) held on the surfaces of the porous polymer may vary according to the proportions of the various monomers (or monomer units), the porosity and pore size of the porous membrane, and the end use thereof. However, it is suitably in the range of about 1–150% by weight based on the weight of the porous membrane, and preferably in the range of about 5–80% by weight. If the amount of crosslinked polymer held is less than the lower limit, it is impossible to impart a sufficient degree of heat resistance, or heat resistance and hydrophilicity, to the porous membrane. On the other hand, amounts greater than the upper limit cannot further improve the hydrophilicity and/or heat resistance of the porous membrane. Rather, excess amount of crosslinked polymer held may be decreased to the volume of each pore of the porous membrane such an extent that the permeation rate of a fluid is reduced.

The amount of crosslinked polymer held is more preferably in the range of about 10–70% by weight and most preferably in the range of about 15–60% by weight.

As described above, the amount of crosslinked polymer held is chosen with consideration for various parameters. For example, in order to meet the need of minimizing shrinkage during heat treatment with steam at 121° C. for 20–30 minutes, the amount of crosslinked polymer held has only to be in the range of about 1–40% by weight. However, especially when a hollow fiber membrane is used under external pressure at high temperatures for a long period of time (for example, to filter hot water above 70° C. for a long period of time), higher filtering pressures may cause a collapse or flattening of the hollow fibers and hence a reduction in permeation performance with time. Accordingly, if the porous membrane is to be used at such high temperatures and high filtering pressure for a long period of time, the amount of crosslinked polymer held should preferably be greater.

No particular limitation is placed on the proportions of the monomers used in the practice of the present invention.

In the case of crosslinked polymers composed of a styrene monomer (St) and divinylbenzene (DVB), the weight ratio of St to DVB (i.e., the St/DVB weight ratio) may range from about 98/2 to about 2/98. In other types of crosslinked polymers, the molar ratio of St to DVB (i.e., the St/DVB molar ratio) may be 1/20 or greater, and the molar ratio of the sum of St and DVB to the polymerizable monomer A (or monomer units D) [i.e., the (St+DVB)/A (or D) molar ratio] may range from about 1/1 to about 2/1 and preferably from about 1/1 to about 1.5/1.

As described above, the heat-resisting porous membrane has a heat-resisting crosslinked polymer (i) held on the surfaces thereof and the hydrophilized porous membrane has a heat-resisting and hydrophilic crosslinked polymer (ii) held on the surfaces thereof. However, a porous membrane exhibiting a combination of heat resistance and hydrophilicity can also be produced by holding a heat-resisting crosslinked polymer (i) and a hydrophilic crosslinked polymer (iii) on the pore walls and/or outer surfaces of the porous membrane in stacked relationship.

Thus, the present invention also provides a hydrophilized porous membrane in which a crosslinked polymer composed principally of a styrene monomer and divinylbenzene is held on at least a part of the surfaces of a porous polyethylene or polypropylene membrane and, in addition, a hydrophilic crosslinked polymer composed principally of a hydrophilic monomer and a crosslinkable monomer is held thereon.

Furthermore, the present invention also provides a process for the production of a hydrophilized heat-resisting porous membrane which comprises the steps of holding a monomer mixture composed principally of a styrene monomer and divinylbenzene, on at least a part of the surfaces of a starting porous membrane formed of polyethylene or polypropylene; thermally polymerizing the monomer mixture; holding a monomer mixture composed principally of a hydrophilic monomer and a crosslinkable monomer, on at least a part of the surfaces of the resulting porous membrane; and thermally polymerizing the monomer mixture.

As the hydrophilic crosslinked polymer, there may be used any conventional hydrophilic crosslinked polymers. One preferred example thereof is a polymer containing 50% by weight or more of diacetone acrylamide as a monomer component, which is disclosed in U.S. Pat. No. 4,695,592.

Although the total amount of the crosslinked polymers (i) and (iii) held in stacked relationship may vary according to the porosity and pore size of the porous membrane, it is preferably in the range of about 5–80% by weight, more preferably in the range of about 10–70% by weight and most preferably in the range of about 15–60% by weight, based on the weight of the porous membrane. The weight ratio of the heat-resisting crosslinked polymer (i) to the hydrophilic crosslinked polymer (iii) is not limited and may be suitably chosen so as to achieve the desired heat resistance and hydrophilicity.

Now, the process for the production of heat-resisting porous membranes in accordance with the present invention will be described hereinafter.

In the practice of the present invention, various methods can be employed to hold a crosslinked polymer on the surfaces of a starting porous membrane. By way of example, a solution is prepared by dissolving monomers and, if necessary, a polymerization initiator in a suitable solvent. Then, a starting porous membrane is impregnated with the solution by immersing the starting porous membrane in the solution or by fabricating a membrane module from the starting porous membrane and causing the solution to penetrate thereinto under pressure. After the solvent is evaporated, the monomers are polymerized. The use of a solution prepared by diluting the monomers with a solvent makes it possible to cause the monomers to adhere substantially evenly to the entire surfaces of the porous membrane without plugging the pores thereof. Moreover, the amounts of the monomers adhering to the surfaces of the porous membrane can be controlled by varying the concentrations of the monomers in the solution or the immersion time.

The solvent used for the preparation of the aforesaid solution is an organic solvent which has a lower boiling point than the monomers and which can dissolve the monomers. Where a polymerization initiator is used, it is preferable to use a solvent which can also dissolve the polymerization initiator.

Useful organic solvents include alcohols such as methanol, ethanol, propanol and isopropanol; ketones such as acetone, methyl ethyl ketone and methyl isobutyl ketone; ethers such as tetrahydrofuran and dioxane; ethyl acetate; and chloroform.

Although no particular limitation is imposed on the boiling point of the organic solvent, its boiling point is preferably below about 100° C. and more preferably below about 80° C. because this facilitates removal of the solvent prior to the polymerization step.

The proportions of the monomers and the solvent in the solution may be suitably chosen in view of the type of the solvent, the desired amount of crosslinked polymer held, and other factors. More specifically, the solvent may be used in an amount of about 50-10,000 parts by weight and more preferably about 100-5,000 parts by weight, per 100 parts by weight of the monomers.

The proportions of the monomers in the solution are preferably determined in consideration of the boiling point and vapor pressure of each monomer, the desired amount of crosslinked polymer held, and other factors. For example, where a polymerizable monomer A, styrene and divinylbenzene are used as monomer components, it is preferable to use the low-boiling components, or divinylbenzene (DVB) and styrene (St), in proportions higher than those desired in the resulting crosslinked polymer. In other words, the (DVB+St)/A molar ratio of the monomers in the solution should preferably range from about 1/1 to about 10/1.

Once the combination of monomers is determined, the proportions of the monomers in the crosslinked polymer are determined on the basis of their reactivity ratios. Accordingly, if the proportion of (DVB+St) is increased, the amount of crosslinked polymer held depends on the concentration of the polymerizable monomer A being a high-boiling component. This makes it possible to control the amount of crosslinked polymer held.

When a starting porous membrane is subjected to an immersion or penetration treatment using a solution as described above, the immersion or penetration time may range from about 0.5 second to about 30 minutes. As the wetting characteristics of the solution for the porous membrane become better, this treatment can be effected in a shorter period of time.

After the monomers and, if present, the polymerization initiator are held on at least a part of the surfaces of the porous membrane in the above-described manner, any excess solution is removed from the periphery of the porous membrane and, if necessary, the solvent present in the pores is evaporated. Then, the porous membrane is subjected to a subsequent polymerization step.

If the temperature employed to evaporate the solvent is excessively high, the polymerization proceeds in part while the solvent still remains. Then, the polymerization takes place off the pore walls of the porous membrane, rather than on the pore walls thereof, so that part of the pores may become plugged. In view of this possible problem, it is preferable to keep the temperature within the range of about 10-50° C. during the removal of the solvent.

In the practice of the present invention, there may be employed any of various polymerization techniques including thermal polymerization, photopolymerization, and radiation polymerization. The polymerization initiator can be any of conventional polymerization initiators.

In photopolymerization, ultraviolet or visible light may be used for purposes of irradiation. As ultraviolet light sources, there may be used low-pressure mercury vapor lamps, high-pressure mercury vapor lamps, xenon lamps, and arc lamps. In radiation polymerization, the monomers can be polymerized, for example, by means of an electron beam irradiation apparatus.

In thermal polymerization, it is desirable that the polymerization temperature be higher than the decomposition temperature of the aforesaid polymerization initiator and not exceed the temperature at which the membrane structure of the porous membrane is changed and the membrane matrix thereof is damaged. Generally the thermal polymerization can be carried out at a temperature of about 30-100° C. Although the heating time depends on the type of the polymerization initiator and the heating temperature, it generally ranges from about 1 minute to about 5 hours and preferably from about 15 minutes to about 3 hours in a batch process. In a continuous process, the polymerization can be effected in a shorter period of time because the heat transfer efficiency is higher. Thus, the heating time generally ranges from about 10 seconds to about 60 minutes and preferably from about 20 seconds to about 10 minutes.

If oxygen is present in the atmosphere for polymerization, the polymerization reaction is significantly inhibited. Accordingly, it is desirable to effect the polymerization in a substantially oxygen-free state, for example, in an atmosphere of an inert gas such as nitrogen gas or in vacuo.

When compared with the two-component polymerization system composed of a styrene monomer and divinylbenzene, the two-component or three-component polymerization system using a polymerizable monomer A as a monomer component has the advantage of providing a significantly higher polymerization rate. Moreover, polymerizable monomers A generally have a high boiling point and exhibit a low vapor pressure at the polymerization temperature. Accordingly, compared with the two-component system composed of a styrene monomer and divinylbenzene, the two-component or three-component system including a polymerizable monomer A is also advantageous in that, when the solution has the same monomer concentration, the amount of crosslinked polymer held in the porous membrane is increased and the yield is improved thereby.

As described above, various polymerization techniques can be employed in the present invention, but it is most preferable to effect the polymerization by means of thermal energy. Since the use of thermal energy permits even the pore portions of the porous membrane to be heated evenly, the monomers can be uniformly polymerized over the entire pore walls on which they are held. Moreover, thermal polymerization is also advantageous in that, if the polymerization temperature is properly chosen, the polymerization can be effected without changing the membrane structure or deteriorating the membrane matrix. By contrast, the use of light energy has the disadvantage that light cannot fully reach the pore portions of the porous membrane owing to scattering thereof. If the irradiation intensity of the light is increased, another disadvantage arises in that the membrane matrix is liable to accelerated deterioration. Similarly, the use of radiation energy also has the disadvantage that the membrane matrix is liable to accelerated deterioration. Accordingly, where these polymerization techniques are employed, it is necessary to carefully choose polymerization conditions which do not cause deterioration of the membrane matrix.

Since the monomers held on the surfaces of the porous membrane are polymerized and crosslinked in situ by any of the above-described polymerization techniques, at least a part of the surfaces of the porous membrane is covered with the resulting crosslinked polymer.

After the crosslinked polymer has been formed, it is desirable to remove any undesired matter (such as unreacted monomers and free polymer) present around the pore walls and outer surfaces of the porous membrane. This can be accomplished by an immersion or penetration treatment using a suitable cleaning solvent, if necessary.

Although the individual steps of the process of the present invention have been separately described above, it should be understood that, in the practice of the present invention, the steps of holding monomers on the surfaces of a starting porous membrane, removing the solvent, polymerizing the monomers, and cleaning the resulting porous membrane can be carried out in a substantially continuous manner.

Now, the process for the production of hydrophilized porous membranes in accordance with the present invention will be described hereinafter.

Hydrophilized porous membranes can be produced by holding a crosslinked polymer (i) on at least a part of the surfaces of a porous polyolefin membrane in the same manner as described on the production of heat-resisting porous membranes, and then hydrolyzing at least a part of the acid anhydride groups or carboxylate groups present in the crosslinked polymer to introduce carboxyl groups thereinto.

In the resulting polymer, the polymerizable monomer A is substantially uniformly distributed on a molecular level because the polymerizable monomer A has high reactivity with divinylbenzene and the styrene monomer, and exhibits a significantly higher reaction rate compared with the polymerization reaction of divinylbenzene and the styrene monomer. Moreover, the acid anhydride groups or carboxylate groups present in the polymerizable monomer A can be easily hydrolyzed into carboxyl groups. Thus, the crosslinked polymer can be easily rendered hydrophilic.

In order to achieve uniform hydrolysis of the crosslinked polymer held on the surfaces of the porous membrane, it is preferable to apply heat to the porous membrane. In this case, the thermal and chemical stability of the polyolefin and the crosslinked polymer held must be taken into consideration. For this reason, it is preferable to immerse the porous membrane in a solution prepared by dissolving, for example, an alkaline substance in a solvent system having low surface tension. Useful alkaline substances include alkali metal hydroxides such as sodium hydroxide, potassium hydroxide and lithium hydroxide, alkali metal carbonates, and ammonia. The concentration of the alkaline substance may be in the range of about 0.1-2N. The solvent can be selected from methanol, ethanol, isopropanol and mixtures of such an alcohol and water. The immersion time may be 5 minutes or longer.

Where a heat-resisting crosslinked polymer (i) and a hydrophilic crosslinked polymer (iii) are held on the pore walls and/or outer surfaces of a starting porous membrane in stacked relationship, the steps extending from immersion into a solution to thermal polymerization of the monomers are repeated twice.

The present invention is further illustrated by the following examples.

In all of these examples, porous membranes obtained by melt forming and subsequent stretching process and having a structure in which slit-like spacings (pores) formed by microfibrils and knots communicated three-dimensionally with one another were used as starting porous membranes.

The amount of crosslinked polymer held was determined by a fractional dissolution method in which the matrix of a porous membrane was dissolved in boiling xylene under reflux, and expressed as a weight percentage of the porous membrane. Heat shrinkage was measured by treating a porous membrane with steam at 121° C. for 30 minutes and comparing its lengths before and after the treatment. Water permeability and water penetration pressure were measured by the following methods, using test membrane modules having an effective membrane area of 163 cm$^2$:

(1) Water permeability:

From one side (the inside of hollow fibers in the case of a hollow fiber membrane) of a test membrane module, ethanol was fed under pressure at a flow rate of 25 ml/min for 15 minutes to wet the porous membrane fully with ethanol to the interior of its pores. Thereafter, water was caused to flow at a flow rate of 100 ml/min for 15 minutes, so that the ethanol contained in the pores was replaced by water. Then, water at 25° C. was caused to flow from one side (the inside of hollow fibers in the case of a hollow fiber membrane) of the test membrane module and the quantity of permeated water was measured at an transmembrane pressure difference of 50 mmHg. The water permeability (in $1/m^2 \cdot hr \cdot mmHg$) was determined from the measured quantity of permeated water.

(2) Water penetration pressure:

Water at 25° C. was fed from one side (the inside of hollow fibers in the case of a hollow fiber membrane) of a test membrane module while the water pressure was raised at a rate of 0.1 kg/cm$^2$ per minute. Thus, water pressures were separately measured when the cumulative quantity of permeated water reached 30 ml and 50 ml. These data were plotted with the water pressure as abscissa and the quantity of permeated water as ordinate, and a straight line connecting these two points was drawn. The pressure at which this straight line intersected the abscissa axis was determined and regarded as the water penetration pressure. (3) Pressure resistance:

Pressure resistance was measured only for porous membranes having the form of hollow fibers. Water at 90° C. was passed through a porous membrane while the filtering pressure was raised at a rate of 0.5 kg/cm$^2$ per minute by the application of external pressure. Thus, the filtering pressure at the point (point A in FIG. 1) where the filtering pressure dependence of the water permeability showed an abrupt change was determined and regarded as the pressure resistance.

(4) Pressure resistance characteristics with time:

Pressure resistance characteristics with time were measured only for porous membranes having the form of hollow fibers. Water at 90° was passed through a porous membrane for an hour while the filtering pressure was adjusted to 3 kg/cm$^2$ by the application of external pressure. Thus, changes in the quantity of permeated water with time were measured. On the basis of the values thus obtained, changes in water permeability (in l/m$^2$·hr·mmHg) with time were determined.

EXAMPLE 1-5

As the starting porous membrane, there was used a porous membrane formed of polyethylene and having a porosity of 65%, a membrane thickness of 70 μm, an elongation at break of 67%, a heat shrinkage of 41% and a water permeability of 1.2 l/m$^2$·hr·mmHg as measured by the alcohol-dependent hydrophilizing method.

This porous membrane was immersed for 10 seconds in the acetone solutions containing styrene, divinylbenzene and maleic anhydride at the respective concentrations shown in Table 1 and further containing 0.2% by weight of benzoyl peroxide. Thereafter, the porous membrane was air-dried at room temperature for 30 minutes to evaporate the acetone, and then heated in an atmosphere of nitrogen gas at 60° C. for 20 minutes to polymerize the monomers. Thus, there was obtained a porous membrane having a crosslinked polymer held on the pore walls thereof. After completion of the polymerization, the porous membrane was ultrasonically cleaned in acetone for 5 minutes and then in warm water for 5 minutes.

The porous membranes thus obtained were evaluated to determine their amount of crosslinked polymer held, elongation at break, water permeability and heat shrinkage. The results are given in Table 1.

When the condensate of steam used for the measurement of heat shrinkage was analyzed with an ultraviolet spectrophotometer, no dissolved component was detected.

The reactivity ratios of the styrene/maleic anhydride system are $r_1 = 0.01$ and $r_2 = 0$.

EXAMPLES 6-11

As the starting porous membrane, there was used a porous hollow fiber membrane formed of polyethylene and having a porosity of 70%, a membrane thickness of 55 μm, an inner diameter of 270 μm, an elongation at break of 43%, a heat shrinkage of 45% and a water permeability of 4.5 l/m$^2$·hr·mmHg as measured by the alcohol-dependent hydrophilizing method.

While this porous membrane was being fed continuously, it was immersed for 12 seconds in the acetone solutions containing styrene, divinylbenzene and maleic anhydride at the respective concentrations shown in Table 1 and further containing 0.2% by weight of bis(4-t-butylcyclohexyl) peroxydicarbonate (Percadox 16; a product of Kayaku-Nooley Co., Ltd.). Thereafter, the monomers were polymerized by allowing the porous membrane to travel through a heating chamber at 85° C. for 5 minutes while passing nitrogen gas therethrough at a flow rate of 3 l/min. Thus, there was obtained a porous membrane having a crosslinked polymer held on the pore walls thereof. After completion of the polymerization, the porous membrane was ultrasonically cleaned in acetone for 5 minutes and then in warm water for 5 minutes.

The porous membranes thus obtained were evaluated to determine their amount of crosslinked polymer held, elongation at break, water permeability and heat shrinkage. The results are given in Table 1.

EXAMPLES 12-17

Porous membranes having a crosslinked polymer held on the pore walls thereof were produced in the same manner as in Example 6 except that, in place of maleic anhydride, di-n-butyl fumarate was used in each of the amounts shown in Table 1. The results of evaluation of these porous membranes are given in Table 1.

The reactivity ratios of the styrene/di-n-butyl fumarate system are $r_1 = 0.15$ and $r_2 = 0$.

EXAMPLES 18-20

As the starting porous membrane, there was used a porous hollow fiber membrane formed of polypropylene and having a porosity of 40%, a membrane thickness of 22 μm, an inner diameter of 200 μm, an elongation at break of 102%, a heat shrinkage of 28% and a water permeability of 0.24 l/m$_2$·hr·mmHg as measured by the alcohol-dependent hydrophilizing method.

While this porous membrane (in the form of a bundle of hollow fibers) was being fed continuously, it was immersed for 12 seconds in the acetone solutions containing styrene, divinylbenzene and maleic anhydride at the respective concentrations shown in Table 1 and further containing 0.3% by weight of 2,2'-azobis(4-methoxy-2,4-dimethylvaleronitrile) (V70; a product of Wako Pure Chemicals Co., Ltd.). Thereafter, the monomers were polymerized by allowing the porous membrane to travel through a heating chamber at 85° C. while passing nitrogen gas therethrough at a flow rate of 3 l/min. Thus, there was obtained a porous membrane having a crosslinked polymer held on the pore walls thereof. After completion of the polymerization, the porous membrane was ultrasonically cleaned in acetone for 5 minutes and then in warm water for 5 minutes.

The porous membranes thus obtained were evaluated to determine their amount of crosslinked polymer held, elongation at break, water permeability and heat shrinkage. The results are given in Table 1.

EXAMPLE 21-24

Porous membranes having a crosslinked polymer held on the pore walls thereof were produced under the same conditions as in Example 1 except that the monomers shown in Table 2 were used. The results of evaluation of these porous membranes are given in Table 2.

EXAMPLE 25-31

Porous membranes having a crosslinked polymer held on the pore walls thereof were produced under the same conditions as in Example 6 except that the monomers shown in Table 2 were used. The results of evaluation of these porous membranes are given in Table 2.

EXAMPLES 32

A porous membrane having a crosslinked polymer held on the pore walls thereof was produced under the same conditions as in Example 18 except that the monomers shown in Table 2 were used. This porous membrane had the performance shown in Table 2.

EXAMPLES 33–37

Porous membranes having a crosslinked polymer held on the pore walls thereof were produced under the same conditions as in each of Examples 1–5. These porous membranes were immersed in a 0.1N solution of sodium hydroxide in ethanol for 3 hours and then washed in running water for 30 minutes.

The porous membranes thus obtained were evaluated to determine their amount of crosslinked polymer held, elongation at break, water permeability, water penetration pressure and heat shrinkage. The results are given in Table 3. When the condensate of steam used for the measurement of heat shrinkage was analyzed with an ultraviolet spectrophotometer, no dissolved component was detected.

EXAMPLES 38–41

Porous membranes having a crosslinked polymer held on the pore walls thereof were produced under the same conditions as in each of Examples 6–9. These porous membranes were immersed in a 0.5N solution of sodium hydroxide in an ethanol-water mixture (in a volume ratio of 95:5) for 5 minutes and then washed in running water for 30 minutes. Thus, there were obtained porous membranes of the present invention to which both heat resistance and hydrophilicity had been imparted as shown in Table 3.

EXAMPLES 42–47

Porous membranes having a crosslinked polymer held on the pore walls thereof were produced under the same condition as in each of Examples 12–17. These porous membranes were treated with a sodium hydroxide solution under the same conditions as in Example 38. Thus, there were obtained porous membranes having the performance shown in Table 3.

EXAMPLES 48 and 49

Porous membranes having a crosslinked polymer held on the pore walls thereof were produced under the same conditions as in each of Examples 19 and 20. These porous membranes were treated with a sodium hydroxide solution under the same conditions as in Example 38. Thus, there were obtained porous membranes having the performance shown in Table 3.

EXAMPLES 50 and 51

Using a hollow fiber forming nozzle in the form of a double cylindrical tube, poly-4-methylpentene-1 (TPXRT18; a product of Mitsui Petrochemical Indsutries, Ltd.) was melt-spun at a spinning temperature of 250° C. and a spinning draft of 500. Then, the spun fiber was subjected to a constant-length heat treatment at 140° C. for 2 minutes, drawn at 25° C. to a stretch ratio of 1.8 and then at 130° C. to a stretch ratio of 2.5, and thermally set at 140° C. while being relaxed to a total stretch ratio of 2.0. Thus, there was obtained a porous hollow fiber membrane having a water permeability of 0.15 l/m$^2$·hr·mmHg as measured by the alcohol-dependent hydrophilizing method, a porosity of 32%, an inner diameter of 250 $\mu$m, a membrane thickness of 20 $\mu$m and a water penetration pressure of 18 kg/cm$^2$.

This porous hollow fiber membrane was being fed continuously in the acetone solutions containing styrene, divinylbenzene and maleic anhydride or di-n-butyl fumarate at the respective concentrations shown in Table 1 and further containing 0.2% by weight of Percadox 16, so that each portion of the fiber was immersed for 12 seconds in the solution. Thereafter, the monomers were polymerized by allowing the porous membrane to travel through a heating chamber at 85° C. for 5 minutes while passing nitrogen gas therethrough at a flow rate of 3 l/min. Thus, there was obtained a porous membrane having a crosslinked polymer held on the pore walls thereof. After completion of the polymerization, the porous membrane was ultrasonically cleaned in acetone for 5 minutes and then in warm water for 5 minutes.

The resulting porous membranes were immersed in a 0.5N solution of sodium hydroxide in an ethanol-water mixture (in a volume ratio of 95:5) for 5 minutes and then washed in water for 30 minutes. Thus, there were obtained porous membranes of the present invention to which both heat resistance and hydrophilicity had been imparted as shown in Table 3.

EXAMPLES 52–54

Using porous polyethylene membranes similar to those used in Example 1, crosslinked polymers were separately held on the pore walls thereof under the same conditions as in Example 1 except that the monomers shown in Table 4 were used. The resulting porous membranes were treated with a sodium hydroxide solution under the same conditions as in Example 33. Thus, there were obtained porous membranes having the performance shown in Table 4.

EXAMPLES 55–57

Using porous polyethylene membranes similar to those used in Example 6, crosslinked polymers were separately held on the pore walls thereof under the same conditions as in Example 6 except that the monomers shown in Table 4 were used. The resulting porous membranes were treated with a sodium hydroxide solution under the same conditions as in Example 38. Thus, there were obtained porous membranes having the performance shown in Table 4.

EXAMPLES 58–60

Porous membranes having a crosslinked polymer held on the pore walls thereof were produced in the same manner as in Example 57 except that, in place of maleic anhydride, di-n-butyl fumarate was used in each of the amounts shown in Table 4. The results of evaluation of these porous membranes are given in Table 4.

EXAMPLES 61 and 62

Using porous polypropylene membranes similar to those used in Example 18, crosslinked polymers were separately held on the pore walls thereof under the same conditions as in Example 18 except that the monomers shown in Table 4 were used. The resulting porous membranes were treated with a sodium hydroxide solution under the same conditions as in Example 38. Thus, there were obtained porous membranes having the performance shown in Table 4.

EXAMPLES 63 and 64

Using porous poly-4-methylpentene-1 membranes similar to those used in Example 50, crosslinked polymers were separately held on the pore walls thereof under the same conditions as in Example 50 except that the monomers shown in Table 4 were used. The resulting porous membranes were treated with a sodium hydroxide solution under the same conditions as in Example 50. Thus, there were obtained porous membranes having the performance shown in Table 4.

EXAMPLES 65–70

As the starting porous membranes, there were used porous hollow fiber membranes formed of polyethylene and having a porosity of 63%, a membrane thickness of 70 μm, an inner diameter of 270 μm and a water permeability of 1.1 l/m$^2$·hr·mmHg as measured by the alcohol-dependent hydrophilizing method.

These porous membranes were immersed for 10 seconds in the solutions consisting of 20 parts of a monomer mixture composed of styrene and divinylbenzene in the corresponding weight ratio shown in Table 5, 0.02 part of benzoyl peroxide and 100 parts of acetone. Thereafter, the porous membrane was taken out of the solution, dried at room temperature for 30 minutes to evaporate the acetone, and then heated in an atmosphere of nitrogen gas at 60° C. for 2 hours to polymerize the monomers. After completion of the polymerization, the porous membrane was ultrasonically cleaned in acetone for 5 minutes and then in warm water for 5 minutes.

The amount of crosslinked polymer held on the thus obtained porous membranes was determined by the fractional dissolution method. Moreover, their water permeability and pressure resistance were measured. The results are given in Table 5.

Furthermore, the above porous membranes were heat-treated with steam at 121° C. for 30 minutes. Thereafter, their morphological structure was observed and their water permeability was measured again.

EXAMPLE 71

As the starting porous membrane, there was used a porous hollow fiber membrane formed of polyethylene and having a porosity of 70%, a membrane thickness of 55 μm, an inner diameter of 270 μm and a water permeability (at 25° C.) of 4.6 l/m$^2$·hr·mmHg as measured by the alcohol-dependent hydrophilizing method. This porous membrane was immersed for 10 seconds in a solution consisting of 25 parts of a monomer mixture composed of styrene and divinylbenzene (in a weight ratio of 50:50), 0.025 part of benzoyl peroxide and 100 parts of acetone. Thereafter, the porous membrane was taken out of the solution, dried at room temperature for 30 minutes to evaporate the acetone, and then heated in an atmosphere of nitrogen gas at 60° C. for 2 hours to polymerize the monomers. After completion of the polymerization, the porous membrane was ultrasonically cleaned in acetone for 5 minutes and then in warm water for 5 minutes.

The porous membrane thus obtained was evaluated to determine their amount of crosslinked polymer held, water permeability and pressure resistance. The results are given in Table 5.

Figure 2:
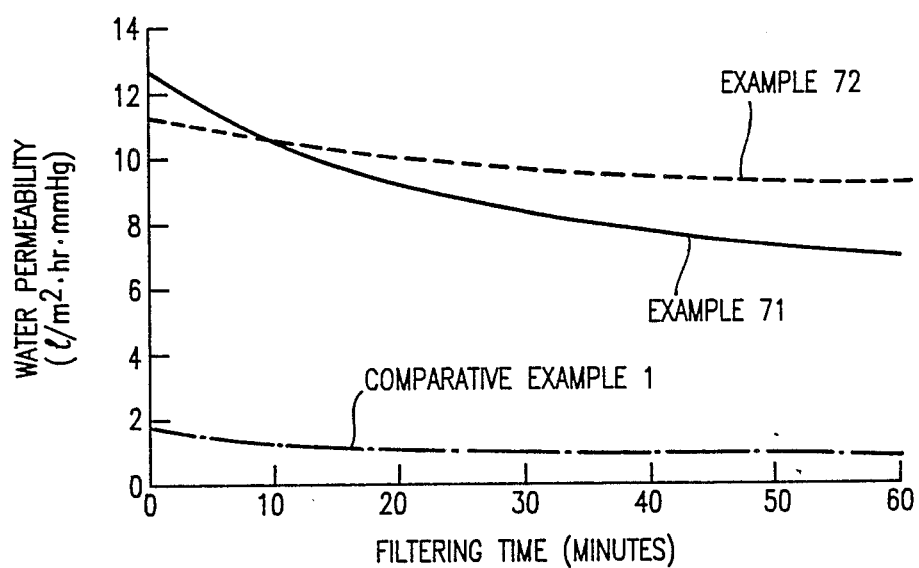
FIG. 2 is a graph illustrating changes in water permeability with time for several porous hollow fiber membranes obtained in the indicated examples and comparative example.

Moreover, when the pressure resistance characteristics with time of this porous membrane were measured, its water permeability showed a slight decreasing tendency (FIG. 2). Furthermore, when this porous membrane was heat-treated with steam at 121° C. for 30 minutes, no morphological change was observed. Its water permeability after the heat treatment was 4.5 l/m$^2$·hr·mmHg, which was equal to the value before the heat treatment.

EXAMPLE 72

A porous membrane having a crosslinked polymer held on the pore walls thereof was produced under the same conditions as in Example 1 except that a solution consisting of 40 parts of a monomer mixture composed of styrene and divinylbenzene (in a weight ratio of 50:50), 0.04 part of benzoyl peroxide and 100 parts of acetone. The porous membrane thus obtained had an amount of crosslinked polymer held of 62.5%, a water permeability of 4.0 l/m$^2$·hr·mmHg and a pressure resistance of 4.5 kg/cm$^2$, and showed good pressure resistance characteristics with time (FIG. 2).

Moreover, when this porous membrane was heat-treated with steam at 121° C. for 30 minutes, no morphological change was observed and its water permeability remained unchanged.

COMPARATIVE EXAMPLE 1

Using a porous polyethylene hollow fiber membrane similar to the starting porous membrane used in Example 71, its pressure resistance and pressure resistance characteristics with time were measured. The pressure resistance was as low as 0.5 kg/cm$^2$, and the pressure resistance characteristics with time were poor as shown in FIG. 2.

Moreover, when this porous membrane was heat-treated with steam at 121° C., it became crimped and its water permeability was reduced to 2.8 l/m$^2$·hr·mmHg.

EXAMPLES 73–77

As the starting porous membrane, there was used a porous hollow fiber membrane formed of polyethylene and having a porosity of 65%, a membrane thickness of 70 μm, an elongation at break of 67%, a heat shrinkage of 41% and a water permeability of 1.2 l/m$^2$·hr·mmHg as measured by the alcohol-dependent hydrophilizing method.

This porous membrane was immersed for 10 seconds in the acetone solutions containing styrene and divinylbenzene at the respective concentrations shown in Table 6 and further containing 0.2% by weight of benzoyl peroxide. Thereafter, the porous membrane was dried at room temperature for 30 minutes to evaporate the acetone, and then heated in an atmosphere of nitrogen gas at 60° C. for 60 minutes to polymerize the monomers. Subsequently, the porous membrane was immersed for 10 seconds in the acetone solutions containing diacetone acrylamide and N-hydroxymethyl acrylamide at the respective concentrations shown in Table 6 and further containing 0.2% by weight of benzoyl peroxide. Thereafter, the porous membrane was taken out of the solution, dried in nitrogen gas for 5 minutes, and then heated in an atmosphere of nitrogen gas at 60° C. for 60 minutes. Then, the porous membrane was immersed for 10 minutes in a water-ethanol mixture (in a weight ratio of 50:50) and ultrasolically cleaned in warm water for 2 minutes to remove any undesired matter. After removing the solvent in a heated atmosphere, there was obtained a porous membrane having a crosslinked polymer held on the surfaces thereof.

The porous membranes thus obtained were evaluated to determine their amount of crosslinked polymer held, elongation at break, water permeability, water penetration pressure and heat shrinkage. The results are given in Table 6. Moreover, when the condensate of steam used for the measurement of heat shrinkage was analyzed with an ultraviolet spectrophotometer, no dissolved component was detected.

In Examples 73–77, water permeability was measured after passing water through the porous membrane under a pressure of 2 kg/cm$^2$ for 3 hours, instead of subjecting it to a pretreatment with ethanol.

TABLE 1

| | Monomer concentrations in solution (wt. %) | | | Molar ratio of (St + DVB) to polymerizable monomer A in solution | Properties of porous membrane obtained | | | | |
|---|---|---|---|---|---|---|---|---|---|
| | St | DVB | Polymerizable monomer A (Note 1) | | Amount of polymer held (g/g) | Elongation at break (%) | Water permeability (1/m$^2$ · hr · mmHg) | Heat shrinkage (%) | Water penetration pressure (kg/cm$^2$) |
| Example 1 | 5 | 5 | MAH 5 | 1.69 | 0.172 | 68 | 1.4 | 4.8 | 1.3 |
| Example 2 | 7 | 7 | MAH 7 | " | 0.205 | 67 | 1.4 | 3.7 | 1.3 |
| Example 3 | 10 | 10 | MAH 7 | 2.42 | 0.208 | 66 | 1.4 | 3.5 | 1.4 |
| Example 4 | 3 | 17 | MAH 7 | 2.23 | 0.232 | 61 | 1.3 | 4.8 | 1.2 |
| Example 5 | 17 | 3 | MAH 7 | 2.61 | 0.213 | 67 | 1.3 | 4.5 | 1.2 |
| Example 6 | 5 | 5 | MAH 5 | 1.69 | 0.210 | 42 | 4.7 | 4.3 | 4.5 |
| Example 7 | 7 | 7 | MAH 7 | " | 0.250 | 42 | 4.7 | 4.0 | 4.5 |
| Example 8 | 10 | 10 | MAH 7 | 2.42 | 0.255 | 42 | 4.7 | 4.0 | 4.5 |
| Example 9 | 3 | 17 | MAH 7 | 2.23 | 0.273 | 40 | 4.6 | 3.9 | 4.4 |
| Example 10 | 17 | 3 | MAH 7 | 2.61 | 0.280 | 37 | 4.5 | 3.8 | 4.4 |
| Example 11 | 20 | 20 | MAH 10 | 3.41 | 0.606 | 25 | 2.2 | 3.5 | 2.1 |
| Example 12 | 5 | 5 | DBF 5 | 4.05 | 0.172 | 42 | 4.7 | 4.6 | 4.5 |
| Example 13 | 7 | 7 | DBF 7 | " | 0.240 | 42 | 4.7 | 4.0 | 4.5 |
| Example 14 | 10 | 10 | DBF 7 | 5.71 | 0.242 | 42 | 4.7 | 4.0 | 4.5 |
| Example 15 | 3 | 17 | DBF 7 | 5.33 | 0.247 | 42 | 4.7 | 4.5 | 4.5 |
| Example 16 | 17 | 3 | DBF 7 | 6.19 | 0.235 | 42 | 4.7 | 4.5 | 4.5 |
| Example 17 | 20 | 20 | DBF 10 | 7.84 | 0.365 | 39 | 4.5 | 4.0 | 4.3 |
| Example 18 | 5 | 5 | MAH 5 | 1.69 | 0.068 | 102 | 0.25 | 2.0 | 0.15 |
| Example 19 | 20 | 20 | MAH 10 | 3.41 | 0.173 | 102 | 0.20 | 4.2 | 0.18 |
| Example 20 | 30 | 10 | MAH 10 | 3.56 | 0.142 | 102 | 0.21 | 4.5 | 0.19 |

(Note 1)
MAH: Maleic anhydride
DBF: Di-n-butyl fumarate

TABLE 2

| | Monomer concentrations in solution (wt. %) | | Molar ratio of (St + DVB) to polymerizable monomer A in solution | Properties of porous membrane obtained | | | | |
|---|---|---|---|---|---|---|---|---|
| | DVB | Polymerizable monomer A | | Amount of polymer held (g/g) | Elongation at break (%) | Water permeability (1/m$^2$ · hr · mmHg) | Heat shrinkage (%) | Water penetration pressure (kg/cm$^2$) |
| Example 21 | 10 | MAH 5 | 1.51 | 0.173 | 68 | 1.4 | 4.8 | 1.3 |
| Example 22 | 10 | MAH 7 | 1.08 | 0.208 | 67 | 1.4 | 3.7 | 1.3 |
| Example 23 | 14 | MAH 7 | 1.51 | 0.250 | 67 | 1.3 | 3.5 | 1.2 |
| Example 24 | 20 | MAH 7 | 2.16 | 0.330 | 67 | 1.3 | 3.0 | 1.2 |
| Example 25 | 10 | MAH 5 | 1.51 | 0.250 | 42 | 4.7 | 4.5 | 4.5 |
| Example 26 | 14 | MAH 7 | 1.08 | 0.330 | 41 | 4.7 | 4.3 | 4.5 |
| Example 27 | 20 | MAH 7 | 2.16 | 0.350 | 40 | 4.6 | 4.2 | 4.5 |
| Example 28 | 40 | MAH 10 | 3.01 | 0.450 | 42 | 4.5 | 3.0 | 4.3 |
| Example 29 | 10 | DBF 5 | 3.62 | 0.240 | 42 | 4.6 | 4.6 | 4.6 |
| Example 30 | 14 | DBF 7 | 3.62 | 0.340 | 42 | 4.5 | 4.0 | 4.5 |
| Example 31 | 20 | DBF 7 | 5.18 | 0.348 | 42 | 4.5 | 3.8 | 4.5 |
| Example 32 | 40 | MAH 10 | 3.01 | 0.173 | 102 | 0.19 | 4.5 | 0.18 |

TABLE 3

| | Monomer concentrations in solution (wt. %) | | | Molar ratio of (St + DVB) to polymerizable monomer A in solution | Properties of porous membrane obtained | | | | |
|---|---|---|---|---|---|---|---|---|---|
| | St | DVB | Polymerizable monomer A | | Amount polymer held (g/g) | Elongation at break (%) | Water permeability (1/m$^2$ · hr · mmHg) | Heat shrinkage (%) | Water penetration pressure (kg/cm$^2$) |
| Example 33 | 5 | 5 | MAH 5 | 1.69 | 0.222 | 68 | 1.4 | 4.8 | 0.8 |
| Example 34 | 7 | 7 | MAH 7 | " | 0.264 | 67 | 1.4 | 3.7 | 0.6 |
| Example 35 | 10 | 10 | MAH 7 | 2.42 | 0.268 | 66 | 1.4 | 3.5 | 0.6 |
| Example 36 | 3 | 17 | MAH 7 | 2.23 | 0.299 | 61 | 1.3 | 4.8 | 0.5 |
| Example 37 | 17 | 3 | MAH 7 | 2.61 | 0.275 | 67 | 1.3 | 4.5 | 0.6 |
| Example 38 | 5 | 5 | MAH 5 | 1.69 | 0.271 | 42 | 4.7 | 4.3 | 0.4 |
| Example 39 | 7 | 7 | MAH 7 | " | 0.323 | 42 | 4.7 | 4.0 | 0.2 |
| Example 40 | 10 | 10 | MAH 7 | 2.42 | 0.329 | 42 | 4.7 | 4.0 | 0.2 |
| Example 41 | 3 | 17 | MAH 7 | 2.23 | 0.352 | 40 | 4.6 | 3.9 | 0.2 |
| Example 42 | 5 | 5 | DBF 5 | 4.05 | 0.137 | 42 | 4.7 | 4.6 | 0.7 |
| Example 43 | 7 | 7 | DBF 7 | " | 0.192 | 42 | 4.7 | 4.0 | 0.5 |
| Example 44 | 10 | 10 | DBF 7 | 5.71 | 0.194 | 42 | 4.7 | 4.0 | 0.5 |
| Example 45 | 3 | 17 | DBF 7 | 5.33 | 0.199 | 42 | 4.7 | 4.5 | 0.4 |
| Example 46 | 17 | 3 | DBF 7 | 6.19 | 0.188 | 42 | 4.7 | 4.5 | 0.5 |

TABLE 3-continued

| | Monomer concentrations in solution (wt. %) | | | Molar ratio of (St + DVB) to polymerizable monomer A in solution | Properties of porous membrane obtained | | | | |
|---|---|---|---|---|---|---|---|---|---|
| | | | | | Amount polymer held (g/g) | Elongation at break (%) | Water permeability (1/m² · hr · mmHg) | Heat shrinkage (%) | Water penetration pressure (kg/cm²) |
| | St | DVB | Polymerizable monomer A | | | | | | |
| Example 47 | 20 | 20 | DBF 10 | 7.84 | 0.293 | 39 | 4.5 | 4.0 | 0.2 |
| Example 48 | 20 | 20 | MAH 10 | 3.41 | 0.223 | 102 | 0.20 | 4.2 | 0.8 |
| Example 49 | 30 | 10 | MAH 10 | 3.56 | 0.184 | 102 | 0.21 | 4.5 | 0.8 |
| Example 50 | 30 | 30 | MAH 10 | 5.18 | 0.141 | — | 0.12 | — | 0.8 |
| Example 51 | 25 | 25 | DBF 25 | 3.79 | 0.160 | — | 0.11 | — | 0.8 |

TABLE 4

| | Monomer concentrations in solution (wt. %) | | Molar ratio of (St + DVB) to polymerizable monomer A in solution | Properties of porous membrane obtained | | | | |
|---|---|---|---|---|---|---|---|---|
| | | | | Amount of polymer held (g/g) | Elongation at break (%) | Water Permeability (1/m² · hr · mmHg) | Heat shrinkage (%) | Water penetration pressure (kg/cm²) |
| | DVB | Polymerizable monomer A | | | | | | |
| Example 52 | 10 | MAH 5 | 1.51 | 0.185 | 68 | 1.4 | 4.8 | 0.8 |
| Example 53 | 14 | MAH 7 | 1.51 | 0.270 | 67 | 1.4 | 3.7 | 0.6 |
| Example 54 | 20 | MAH 7 | 2.16 | 0.350 | 67 | 1.4 | 3.6 | 0.6 |
| Example 55 | 10 | MAH 5 | 1.51 | 0.270 | 42 | 4.7 | 4.5 | 0.5 |
| Example 56 | 14 | MAH 7 | 1.51 | 0.360 | 41 | 4.6 | 3.3 | 0.4 |
| Example 57 | 20 | MAH 7 | 2.16 | 0.385 | 40 | 4.7 | 3.2 | 0.4 |
| Example 58 | 10 | DBF 5 | 3.62 | 0.263 | 40 | 4.5 | 4.0 | 0.5 |
| Example 59 | 14 | DBF 7 | 3.62 | 0.363 | 41 | 4.5 | 3.5 | 0.3 |
| Example 60 | 20 | DBF 7 | 5.18 | 0.388 | 42 | 4.5 | 3.4 | 0.3 |
| Example 61 | 40 | MAH 10 | 3.01 | 0.185 | 102 | 0.19 | 4.5 | 0.8 |
| Example 62 | 60 | MAH 10 | 4.53 | 0.235 | 102 | 0.19 | 4.4 | 0.8 |
| Example 63 | 60 | MAH 10 | 4.53 | 0.175 | — | 0.12 | — | 0.8 |
| Example 64 | 50 | DBF 25 | 3.62 | 0.160 | — | 0.12 | — | 0.8 |

TABLE 5

| | Monomer concentration in solution (wt. %) | | Weight ratio of St to DVB in solution | Properties of porous membrane obtained | | | After heat treatment | |
|---|---|---|---|---|---|---|---|---|
| | | | | Amount of polymer held (g/g) | Water permeability (1/m² · hr · mmHg) | Pressure resistance (kg/cm²) | Morphological structure | Water permeability (1/m² · hr · mmHg) |
| | St | DVB | | | | | | |
| Example 65 | 18 | 2 | 90/10 | 17.6 | 1.0 | >5.0 | Unchanged | 0.8 |
| Example 66 | 14 | 6 | 70/30 | 19.0 | 1.1 | " | " | 1.0 |
| Example 67 | 6 | 14 | 30/70 | 17.7 | 1.1 | " | " | 1.1 |
| Example 78 | 2 | 18 | 10/90 | 19.1 | 1.0 | " | " | 1.0 |
| Example 69 | 0.4 | 19.6 | 2/98 | 20.5 | 1.0 | 4.0 | " | 1.0 |
| Example 70 | 19.6 | 0.4 | 98/2 | 22.5 | 0.9 | 4.5 | " | 0.9 |
| Example 71 | 10 | 10 | 50/50 | 23.6 | 4.5 | 3.5 | " | 4.5 |
| Example 72 | 14.2 | 14.2 | " | 62.5 | 4.0 | 4.5 | " | 4.0 |
| Comparative Example 1 | — | — | — | — | — | 0.5 | Crimped | 2.8 |

TABLE 6

| | Monomer concentrations in solution (wt. %) | | | | Properties of porous membrane obtained | | | | |
|---|---|---|---|---|---|---|---|---|---|
| Example No. | St | DVB | Hydrophilic monomer | Crosslinkable monomer | Amount of heat-resisting crosslinked polymer held (g/g) | Amount of hydrophilic crosslinked polymer held (g/g) | Elongation at break (%) | Water permeability (1/m² · hr · mmHg) | Heat shrinkage (%) | Water penetration pressure (kg/cm²) |
| Example 73 | 5 | 5 | DAAM 10 | N-HAM 0.5 | 20 | 15 | 68 | 1.4 | 5.0 | 0.3 |
| Example 74 | 7 | 7 | " | N-HAM 0.5 | 25 | 15 | 67 | 1.4 | 4.0 | 0.3 |
| Example 75 | 10 | 10 | " | N-HAM 0.5 | 30 | 15 | 60 | 1.3 | 3.8 | 0.3 |
| Example 76 | 3 | 17 | " | N-HAM 0.5 | 35 | 16 | 63 | 1.2 | 3.5 | 0.3 |
| Example 66 | 0 | 20 | " | N-HAM 0.5 | 35 | 14 | 63 | 1.2 | 4.8 | 0.3 |

(Note)
DAAM: Diacetone acrylamide
N-HAM: N-hydroxymethyl acrylamide

The foregoing examples show that the heat-resisting porous membranes of the present invention have markedly improved heat resistance compared with conventional porous membranes formed of polyethylene or polypropylene. In other words, porous membranes holding a crosslinked polymer in accordance with the present invention show practically no morphological change or reduction in water permeability even after treatment with steam at 121° C.

Moreover, the process of the present invention which employs thermal polymerization can adhere the crosslinked polymer to the pore walls of the porous membrane almost uniformly. Especially where a polymerizable monomer A having a high boiling point is used, the yield of the crosslinked polymer incorporated in the porous membrane is high and the crosslinked polymer can be more uniformly held on the surfaces of the porous membrane. Furthermore, the amount of crosslinked polymer held can be controlled easily.

The hydrophilized porous membranes of the present invention have significantly low water penetration pressure compared with untreated porous polyolefin membranes. Moreover, they have such excellent heat resistance that they show little shrinkage and practically no morphological change even after treatment with steam at 121° C.

Since the process of the present invention provides a high polymerization rate, a crosslinked polymer can be held on the surfaces of a porous polyolefin membrane in a short period of time. Moreover, the resulting porous membrane can be rendered hydrophilic simply by hydrolyzing the crosslinked polymer.

The porous membranes of the present invention can be used in membrane separation process which requires steam sterilization, for example, in such fields as medicine, the food industry and the fermentation industry, and in hot water treatments involved, for example, in the purification of polysaccharides and the treatment of condensate from power stations. Moreover, they can also be used in the cultivation of animals and plants, the separation of proteins by adsorption, membrane chromatography, and other fields.

We claim:

1. A heat-resisting porous membrane comprising a porous polyethylene or polypropylene membrane having a crosslinked polymer held on at least a part of the surfaces thereof, the crosslinked polymer being composed principally of (a) a polymerizable monomer A containing one acid anhydride group or two esterified carboxyl groups and having reactivity ratios $R_1$ and $R_2$ of not greater than 0.30 for copolymerization with styrene, (b) divinylbenzene and optionally (c) at least one of styrene and α-methylstyrene in proportions and under conditions to provide heat resistant properties sufficient to enable said member to effectively withstand wet steam sterilization.

2. A process for the production of a heat-resisting porous membrane, which comprises the steps of:
holding a monomer mixture composed principally of
(a) a polymerizable monomer A as defined above,
(b) divinylbenzene and optionally (c) at least one of styrene and α-methylstyrene, on at least a part of the surfaces of a starting porous membrane formed of polyethylene or propylene; and
thermally polymerizing the monomer mixture in proportions and under conditions to provide heat resistance properties sufficient to enable said membrane to effectively withstand wet steam sterilization.

3. A hydrophilized porous membrane, comprising:
a porous polyolefin membrane having a crosslinked polymer held on at least a part of the surfaces thereof, the crosslinked polymer being composed principally of (d) monomer units D containing at least one carboxyl group, (b) divinylbenzene units and optionally (c) monomer units derived from at least one of styrene and α-methylstyrene in proportions and polymerized under conditions to provide a membrane with heat resistance properties sufficient to enable said membrane to effectively withstand wet steam sterilization, said crosslinked polymer being characterized by a substantial uniform distribution of the monomer units D.

4. A process for the production of a hydrophilized porous membrane, which comprises the steps of:
holding a monomer mixture composed principally of
(a) a polymerizable monomer A as defined above,
(b) divinylbenzene and optionally (c) at least one of styrene and α-methylstyrene, on at least a part of the surfaces of a starting porous membrane formed of a polyolefin;
heating the monomer mixture to form a crosslinked polymer; and
hydrolyzing at least a part of the acid anhydride groups or esterified carboxyl groups present in the crosslinked polymer, said monomers being polymerized in proportions and under conditions to provide heat resistance properties sufficient to enable said membrane to effectively withstand wet steam sterilization.

5. A heat-resisting porous membrane, comprising:
a porous polyethylene or polypropylene membrane having a crosslinked polymer held on at least a part of the surfaces thereof, the crosslinked polymer being composed principally of (b) divinylbenzene and (c) at least one of styrene and α-methylstyrene in proportions to provide heat resistant properties sufficient to enable said membrane to effectively withstand wet steam sterilization.

6. A heat-resisting porous membrane as claimed is claim 5 wherein a hydrophilic crosslinked polymer composed principally of a hydrophilic monomer and a crosslinkable monomer is held on at least a part of the surfaces of the porous polyethylene or polypropylene membrane and/or on the crosslinked polymer.

7. A heat-resisting porous membrane as claimed in claim 6 wherein the hydrophilic monomer is diacetone acrylamide.

8. A process for the production of a heat-resisting porous membrane, which comprises the steps of:
holding a monomer mixture composed principally of (b) divinylbenzene and (c) at least one of styrene and α-methyl styrene, on at least a part of the surfaces of a starting porous membrane formed of polyethylene or polypropylene; and
thermally polymerizing the monomer mixture in proportions and under conditions to provide heat resistant properties sufficient to enable said membrane to effectively withstand wet steam sterilization.

9. A process as claimed in claim 8 which further includes the steps of holding a monomer mixture composed principally of a hydrophilic monomer and a crosslinkable monomer, on at least a part of the surfaces of the resulting porous membrane; and thermally polymerizing the monomer mixture.

* * * * *

UNITED STATES PATENT AND TRADEMARK OFFICE
CERTIFICATE OF CORRECTION

PATENT NO.   :   4,961,853
DATED        :   OCTOBER 9, 1990
INVENTOR(S)  :   HAJIME ITOH ET AL.

It is certified that error appears in the above-identified patent and that said Letters Patent is hereby corrected as shown below:

On the title page, in item [30]:

In the Foreign Application Priority Data, please delete "62-2787341" and insert --62-278734--.

Signed and Sealed this

Seventeenth Day of March, 1992

Attest:

HARRY F. MANBECK, JR.

*Attesting Officer*            *Commissioner of Patents and Trademarks*